US008812075B2

(12) United States Patent
Nguyen et al.

(10) Patent No.: US 8,812,075 B2
(45) Date of Patent: *Aug. 19, 2014

(54) CONTOURED ELECTRODE

(75) Inventors: Tin Nguyen, Livermore, CA (US);
Cheng-I Chuang, San Jose, CA (US);
KooHyoung Lee, San Jose, CA (US);
Jong-Jin Lim, Daejeon (KR)

(73) Assignee: NeuroSky, Inc., San Jose, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 13/620,039

(22) Filed: Sep. 14, 2012

(65) Prior Publication Data

US 2013/0066184 A1 Mar. 14, 2013

Related U.S. Application Data

(63) Continuation of application No. 12/283,613, filed on Sep. 12, 2008, now Pat. No. 8,301,218, which is a continuation-in-part of application No. 10/585,500, filed as application No. PCT/KR2004/001573 on Jun. 29, 2004, now Pat. No. 8,290,563, said application No. 12/283,613 is a continuation-in-part of application No. 11/656,828, filed on Jan. 22, 2007, and a continuation-in-part of application No. 12/116,020, filed on May 6, 2008, now Pat. No. 8,170,637.

(60) Provisional application No. 61/028,258, filed on Feb. 13, 2008.

(30) Foreign Application Priority Data

Jan. 8, 2004 (KR) .......................... 10-2004-001127

(51) Int. Cl.
*A61B 5/0478* (2006.01)

(52) U.S. Cl.
CPC .................................... *A61B 5/0478* (2013.01)
USPC ............ 600/383; 600/544; 600/382; 600/372

(58) Field of Classification Search
CPC .............. A61B 5/0478; A61B 5/0476; A61B 5/04845; A61B 5/0496; A61B 5/4064; A61B 5/6803; A61B 5/6814; A61B 5/6835; A61B 5/7405; A61B 2560/0468; A61B 2560/0487; A61B 2562/0209; A61B 2562/0214; A61B 2562/164; A61B 2562/16; A61B 2562/227
USPC .................. 600/383, 390, 378, 394, 544–545
See application file for complete search history.

(56) References Cited

U.S. PATENT DOCUMENTS 3,508,541 A * 4/1970 Westbrook et al. ........... 600/383
3,669,119 A * 6/1972 Symmes ....................... 607/141

(Continued)

FOREIGN PATENT DOCUMENTS

| JP | 5-48903 | 6/1993 |
| JP | 2003-38454 A | 2/2003 |

(Continued)

*Primary Examiner* — Lee S Cohen
*Assistant Examiner* — Erin M Cardinal
(74) *Attorney, Agent, or Firm* — Van Pelt, Ji & James LLP

(57) ABSTRACT

A contoured bioelectrical signal electrode and a sensor headset are disclosed. A contoured bioelectrical signal electrode that also includes a conductive fabric is also disclosed. In some embodiments, a contoured bioelectrical signal sensor is provided that includes an electrode set and is connected to a holder that is connected to a headset.

23 Claims, 10 Drawing Sheets

(56) References Cited

U.S. PATENT DOCUMENTS

| | | | | |
|---|---|---|---|---|
| 4,781,196 A | * | 11/1988 | Killion | 600/379 |
| 5,169,380 A | * | 12/1992 | Brennan | 600/26 |
| 5,800,351 A | * | 9/1998 | Mann | 600/383 |
| 6,080,110 A | * | 6/2000 | Thorgersen | 600/500 |
| 6,154,669 A | * | 11/2000 | Hunter et al. | 600/383 |
| 6,381,481 B1 | * | 4/2002 | Levendowski et al. | 600/383 |
| 6,574,513 B1 | * | 6/2003 | Collura et al. | 607/122 |
| 8,170,637 B2 | * | 5/2012 | Lee et al. | 600/372 |
| 8,301,218 B2 | * | 10/2012 | Nguyen et al. | 600/383 |
| 8,396,529 B2 | | 3/2013 | Lee et al. | |
| 2001/0044573 A1 | * | 11/2001 | Manoli et al. | 600/383 |
| 2004/0122303 A1 | * | 6/2004 | Kopke | 600/383 |
| 2007/0106169 A1 | * | 5/2007 | Fadem | 600/544 |
| 2007/0112277 A1 | * | 5/2007 | Fischer et al. | 600/544 |
| 2007/0225585 A1 | * | 9/2007 | Washbon et al. | 600/393 |

FOREIGN PATENT DOCUMENTS

| | | | |
|---|---|---|---|
| WO | WO 9714357 A1 * | 4/1997 | A61B 5/024 |
| WO | 99/42032 | 8/1999 | |
| WO | 2008067839 | 6/2008 | |

* cited by examiner

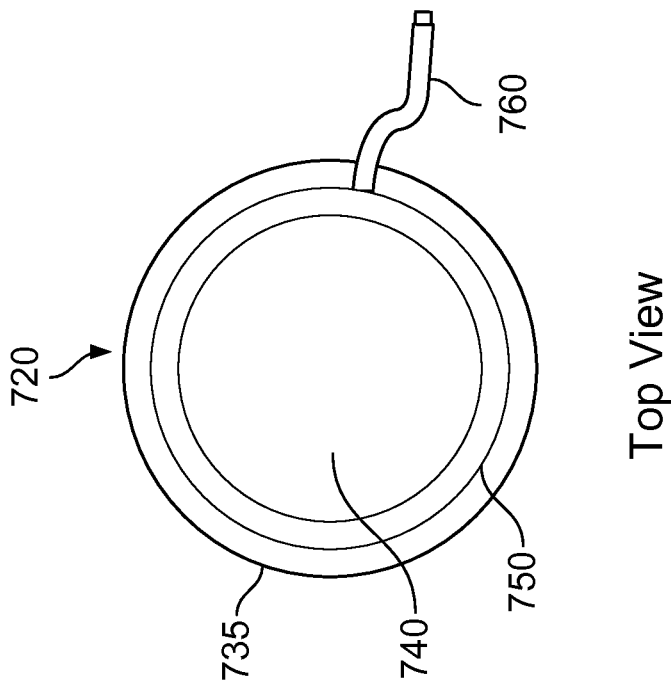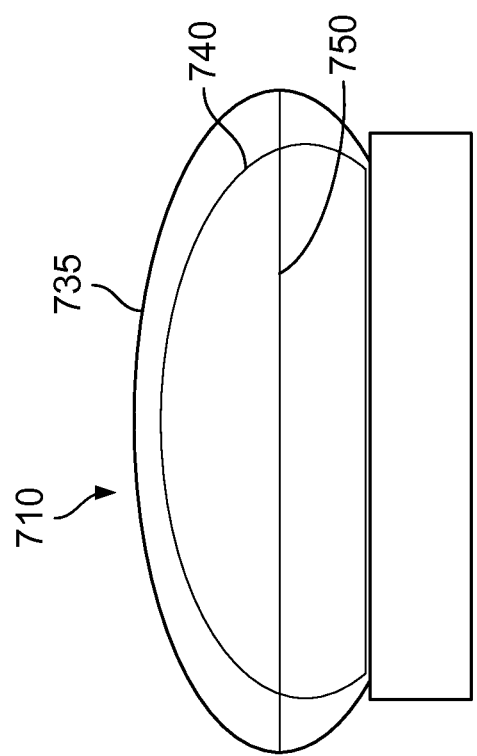
FIG. 7

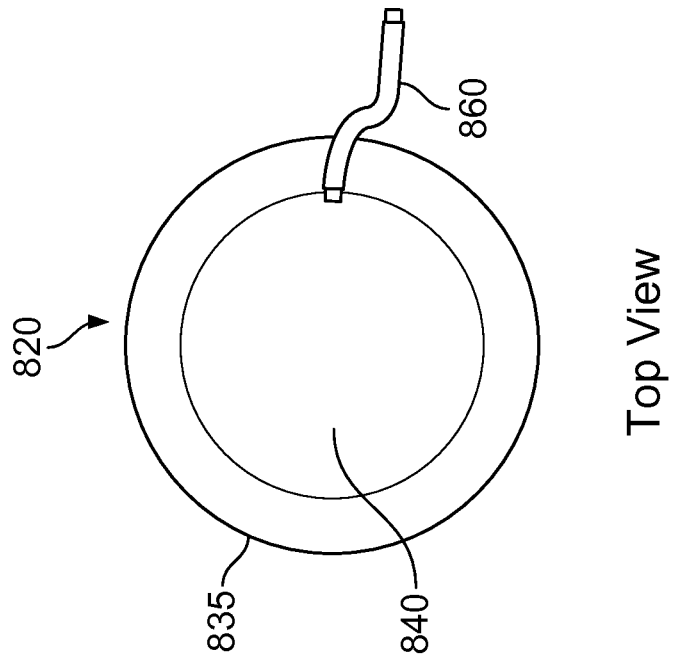
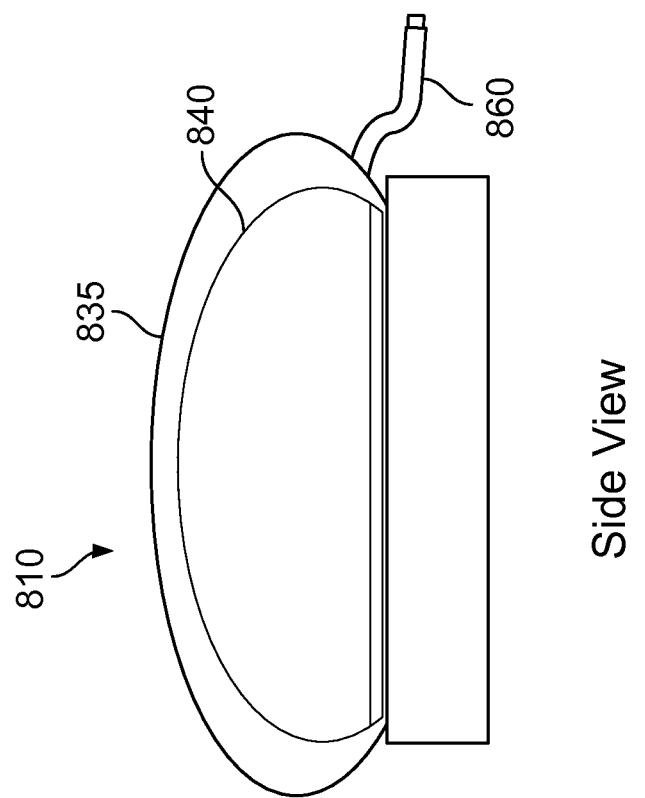
FIG. 8

CONTOURED ELECTRODE

CROSS REFERENCE TO OTHER APPLICATIONS

This application is a continuation of U.S. patent application Ser. No. 12/283,613, now U.S. Pat. No. 8,301,218, entitled CONTOURED ELECTRODE, filed Sep. 12, 2008, which is a continuation in part of U.S. patent application Ser. No. 10/585,500, now U.S. Pat. No. 8,290,563, entitled ACTIVE DRY SENSOR MODULE FOR MEASUREMENT OF BIOELECTRICITY, filed Jul. 3, 2005, with a 371 entry date of Feb. 17, 2009, which claims priority to PCT Application No. PCT/KR04/01573, entitled ACTIVE DRY SENSOR MODULE FOR MEASUREMENT OF BIO-ELECTRICITY, filed Jun. 29, 2004, which claims priority under 35 U.S.C. §119, from Korean Patent Application No. 10-2004-001127, entitled ACTIVE DRY SENSOR MODULE FOR MEASUREMENT OF BIOELECTRICITY, filed on Jan. 8, 2004 in the Korean Intellectual Property Office, and which is incorporated herein by reference for all purposes; continuation in part of co-pending U.S. patent application Ser. No. 11/656,828, entitled METHOD AND APPARATUS FOR QUANTITATIVELY EVALUATING MENTAL STATES, filed Jan. 22, 2007, which is incorporated herein by reference for all purposes; and continuation in part of U.S. patent application Ser. No. 12/116,020, now U.S. Pat. No. 8,170,637, entitled DRY ELECTRODE DEVICE AND METHOD OF ASSEMBLY filed May 6, 2008, which is incorporated herein by reference for all purposes.

This application claims priority to U.S. Provisional Patent Application No. 61/028,258 entitled NEURO-HEADSET DEVICE WITH AUDIO SPEAKERS filed Feb. 13, 2008, which application is incorporated herein by reference for all purposes.

BACKGROUND OF THE INVENTION

Electrodes generally are well known. For example, bioelectrical signal electrodes can be used to measure an electrical signal of the human body, such as a brain wave and muscle action potentials.

BRIEF DESCRIPTION OF THE DRAWINGS

Various embodiments of the invention are disclosed in the following detailed description and the accompanying drawings.

FIG. 7 is another embodiment of a contoured electrode illustrating a side view and a top view of a contoured electrode including a conductive fabric.

FIG. 8 is another embodiment of a contoured electrode illustrating a side view and a top view of a contoured electrode including a conductive fabric.

DETAILED DESCRIPTION

Most of the known electrodes for measuring bioelectrical signals (e.g., brain waves) require special treatments or mechanisms for affixing the electrode to be in close contact with the user's skin and/or the surface of the user's head (for Electroencephalogram, also referred to as EEG). Common electrodes for brain wave signal are flat disk-like apparatus, generally flat but sometimes with spikes to allow the sensor to go through human hair, or with use of a needle to penetrate skin, and/or include a cavity for conductive gel. For example, surface electrodes for measuring brain waves generally are electrodes that are wet with use of conductive gel (e.g., a cavity for conductive gel), needle electrodes, and/or are electrodes that are otherwise affixed to the head using adhesive mechanisms to maintain close contact with the skin/surface of the user's head.

Thus, it is desirable to provide a dry electrode that can maintain close contact with the user's head that does not require the use of these other, relatively invasive, cumbersome, and/or uncomfortable techniques (e.g., gel or wet electrodes, needle or spike electrodes, and/or is adhesive for affixing electrodes to the user's head).

Figure 6:
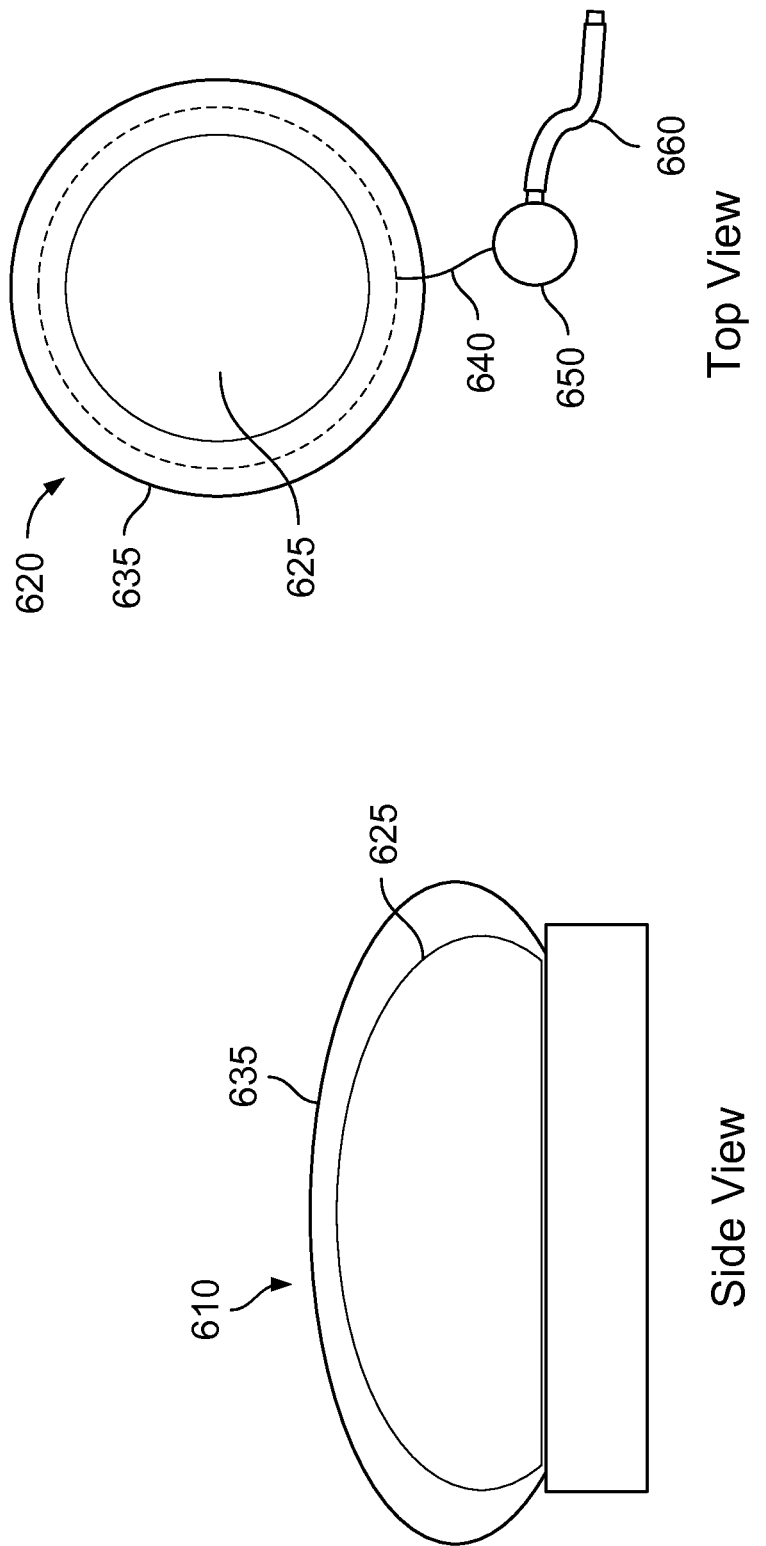
FIG. 6 is an embodiment of a contoured electrode illustrating a side view and a top view of a contoured electrode including a conductive fabric.
Figure 10:
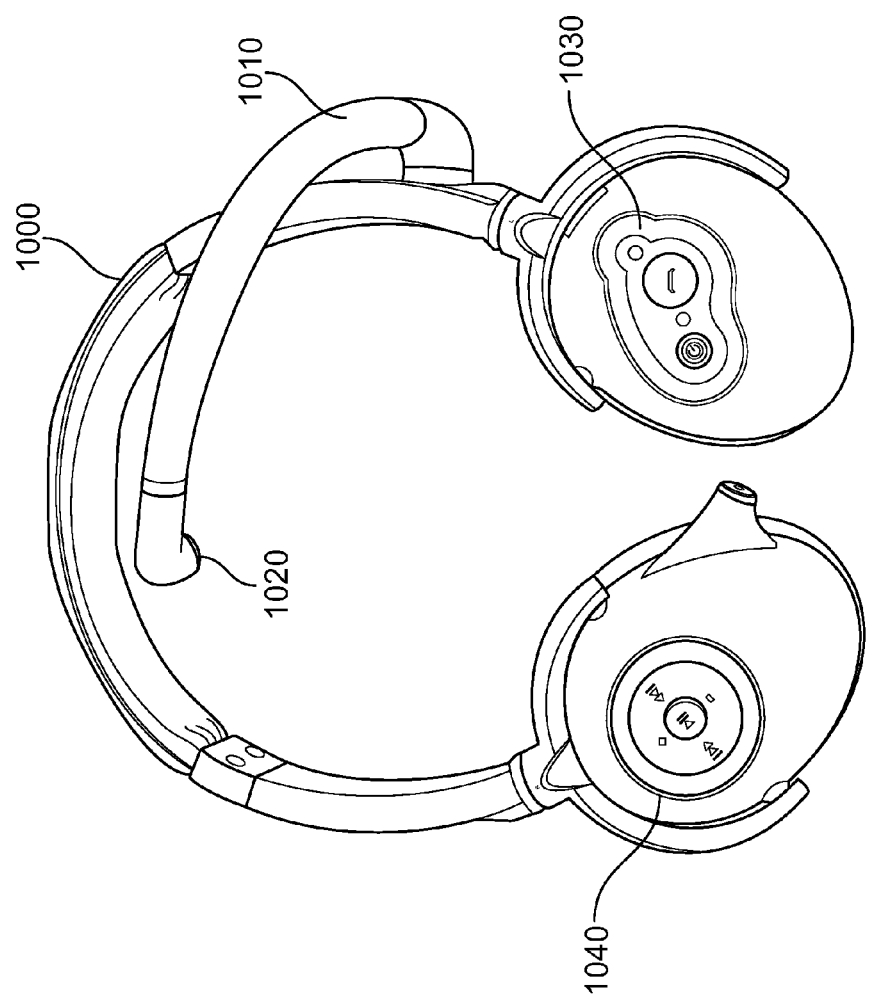
FIG. 10 is an embodiment of a sensor headset.

Accordingly, a bioelectrical signal contoured electrode is disclosed. For example, a contoured bioelectrical signal electrode allows for comfortable and stable skin/head contact to sense bioelectrical signals, as such stable and close contact with the user's skin/head is important for minimizing noise caused by electrode movement and/or an electrode that is not in close contact with the user's skin/head. A contoured electrode also simplifies the design of the electrode holder, such as a headset (e.g., integrated in the earpiece of the headset and/or using an arm integrated in the headset), to fit user body of different size, shape, and contour. For example, a contoured electrode can be maintained in contact with the user's head using a holder (e.g., a flexible forehead sensor arm 610 as shown in FIG. 6), the contoured electrode attached to the end of the flexible holder, which is connected to a headset (e.g., sensor headset 1000 as shown in FIG. 10).

For example, the disclosed contoured electrode is particularly applicable to the electrode structures described and illustrated below for maintaining a surface electrode in contact with a user's skin/head, as described below. It will be appreciated; however, that a contoured electrode set has greater utility since it can be assembled or manufactured with different elements than those described below and be within the scope of the electrode set disclosed herein. It will also be appreciated that the disclosed contoured electrode can be used for any type of bioelectrical signal sensor device, process, and/or application.

In one embodiment, a contoured bioelectrical signal electrode has an electrically conductive surface that is not flat, as it includes a shaped protrusion (e.g., a contoured electrode). The electrical conductivity is due to material the electrode is made of, or coating and platting of electrical conductive material onto the base material. In one embodiment, a contoured electrode includes additional mechanisms to allow for an electrical wire attachment and/or to mount the electrode securely in a sensor, probe, or other sensor related measurement instrument with an electrode holder (e.g., a headset for use with a computer, a portable computing device, a phone, a portable music player, an entertainment system, and/or a video game system).

In one embodiment, a contoured bioelectrical signal electrode is attached to a wire that connects to a bioelectrical signal circuit. The electrode is then fitted to a user's body making is skin contact (e.g., using a sensor headset 1000 as shown in FIG. 10). During the fitting process, using the contour of the electrode, it can be pivoted, rotated or angled in a much wider range of fitting without losing contact, unlike the traditional flat disk sensor of typical electrodes. For example, a contoured bioelectrical signal electrode allows the electrode to fit the wearer's body size and/or shape easily, allowing the electrode to be rotated, pivoted, and angled in a much wider range than allowed with the traditional flat electrodes.

The invention can be implemented in numerous ways. In this specification, these implementations, or any other form that the invention may take, may be referred to as techniques and/or embodiments.

A detailed description of one or more embodiments of the invention is provided below along with accompanying figures that illustrate the principles of the invention. The invention is described in connection with such embodiments, but the invention is not limited to any embodiment. The scope of the invention is limited only by the claims and the invention encompasses numerous alternatives, modifications and equivalents. Numerous specific details are set forth in the following description in order to provide a thorough understanding of the invention. These details are provided for the purpose of example and the invention may be practiced according to the claims without some or all of these specific details. For the purpose of clarity, technical material that is known in the technical fields related to the invention has not been described in detail so that the invention is not unnecessarily obscured.

Figure 1:
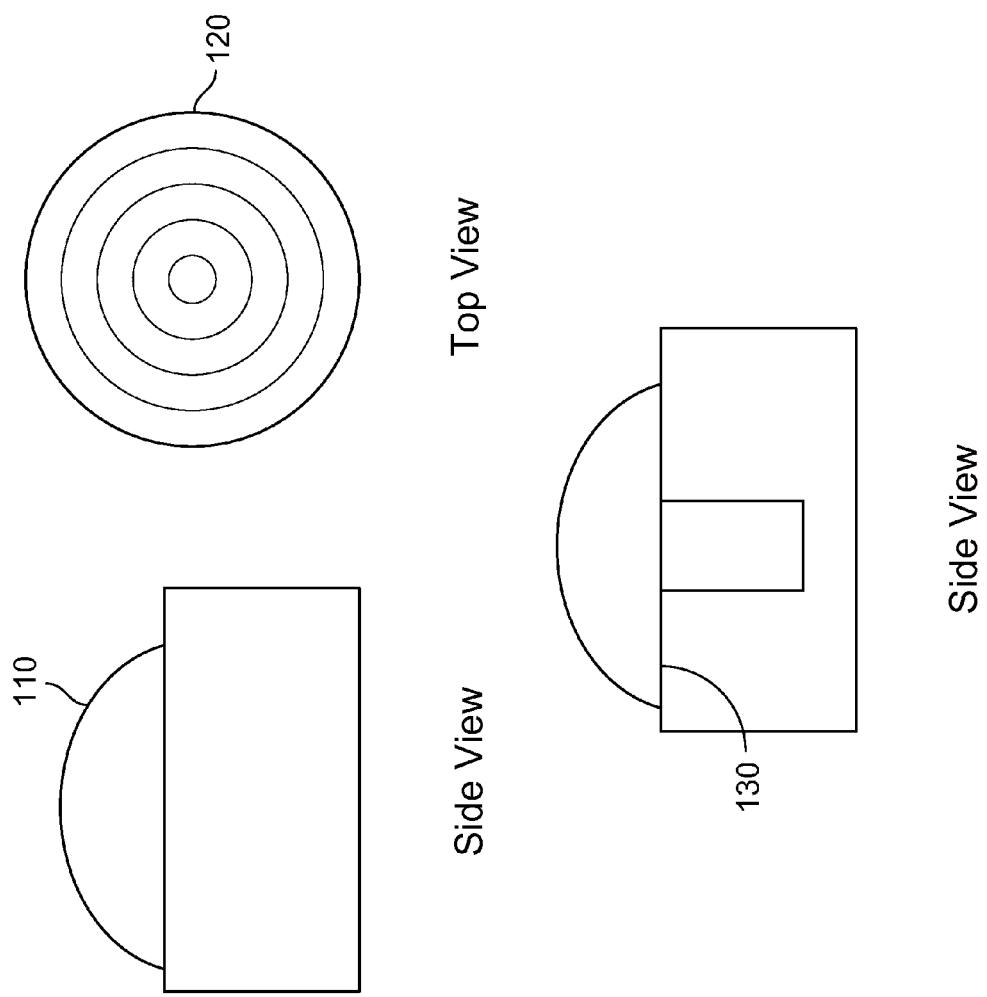
FIG. 1 is an embodiment of a contoured electrode illustrating views of a quarter dome contoured electrode.

FIG. 1 is an embodiment of a contoured electrode illustrating views of a quarter dome contoured electrode. As shown in FIG. 1, a side view 110 of a contoured electrode illustrates the protruding shape of the quarter dome electrode. A top view 120 illustrates a top view of the quarter dome shaped electrode (e.g., a quarter spherical shaped electrode). Another side view 130 illustrates an example of additional structure to allow a wire attachment and physical mounting and attachment to the contoured electrode signal sensor housing.

Figure 2:
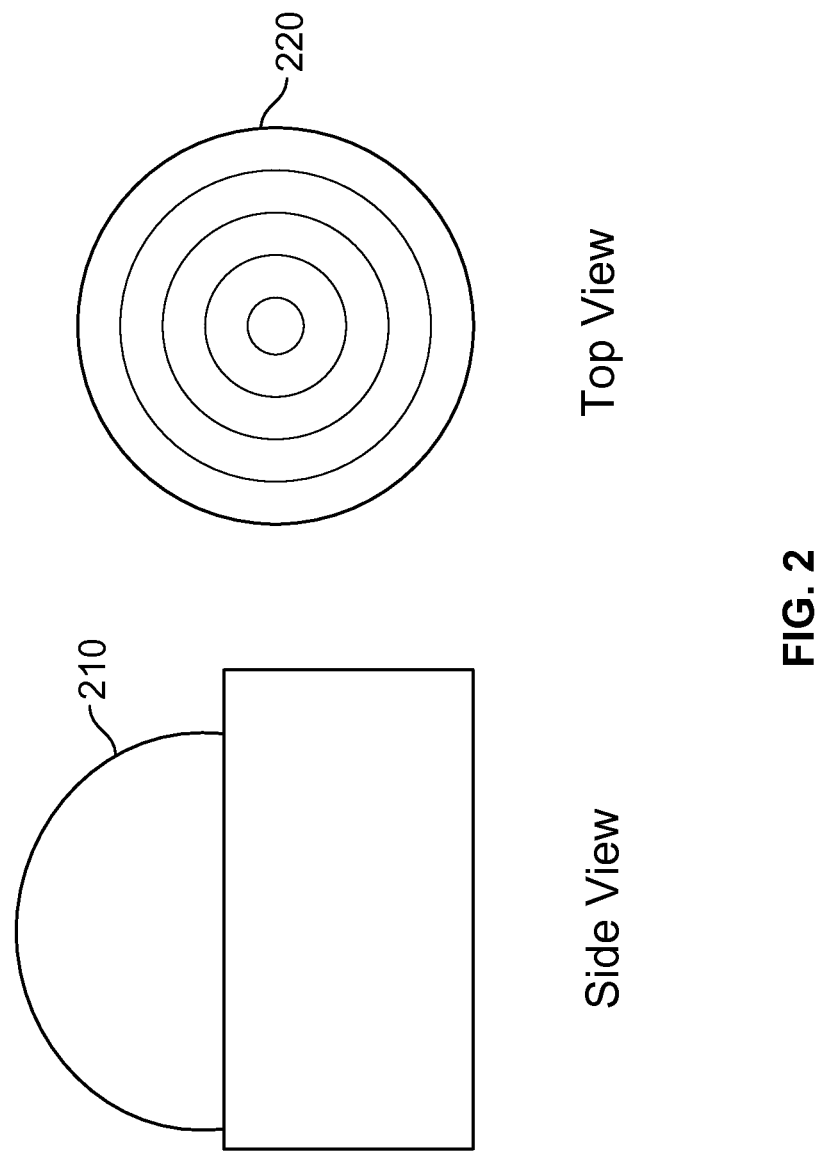
FIG. 2 is an embodiment of a contoured electrode illustrating views of a half dome contoured electrode.

FIG. 2 is an embodiment of a contoured electrode illustrating views of a half dome contoured electrode. As shown in FIG. 2, a side view 210 of a contoured electrode illustrates the protruding shape of the half dome electrode (e.g., half spherical shaped electrode). A top view 220 illustrates a top view of the half dome shaped electrode. In one embodiment, a is contoured electrode includes a spherical shape or some other spherical variant shape that provides a protrusion for maintaining contact with the user's skin/head.

Figure 3:
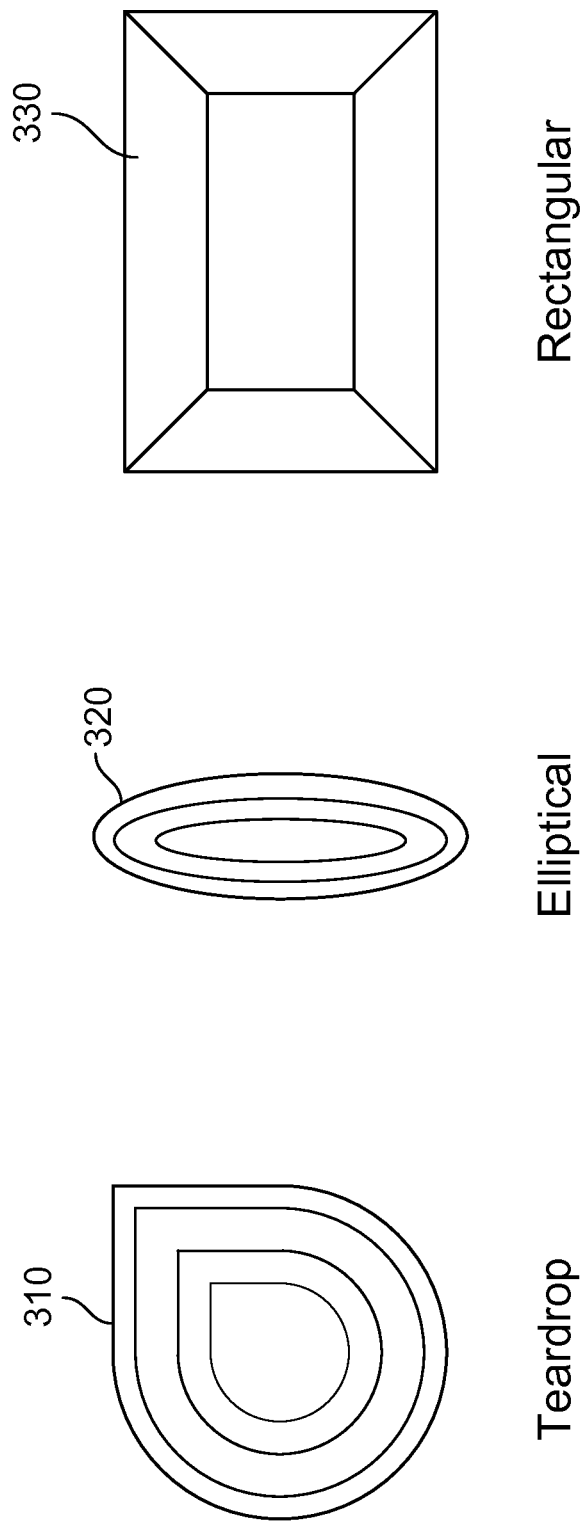
FIG. 3 is an embodiment illustrating various other shapes for a contoured electrode.

FIG. 3 is an embodiment illustrating various other shapes for a contoured electrode. A teardrop shaped electrode 310 is shown as one embodiment of a contoured electrode, which as shown includes a protruding shape. An elliptical shaped electrode 320 is shown as one embodiment of a contoured electrode, which as shown includes a protruding shape. A rectangular shaped electrode 330 is shown as one embodiment of a contoured electrode, which as shown includes a protruding shape.

Figure 4:
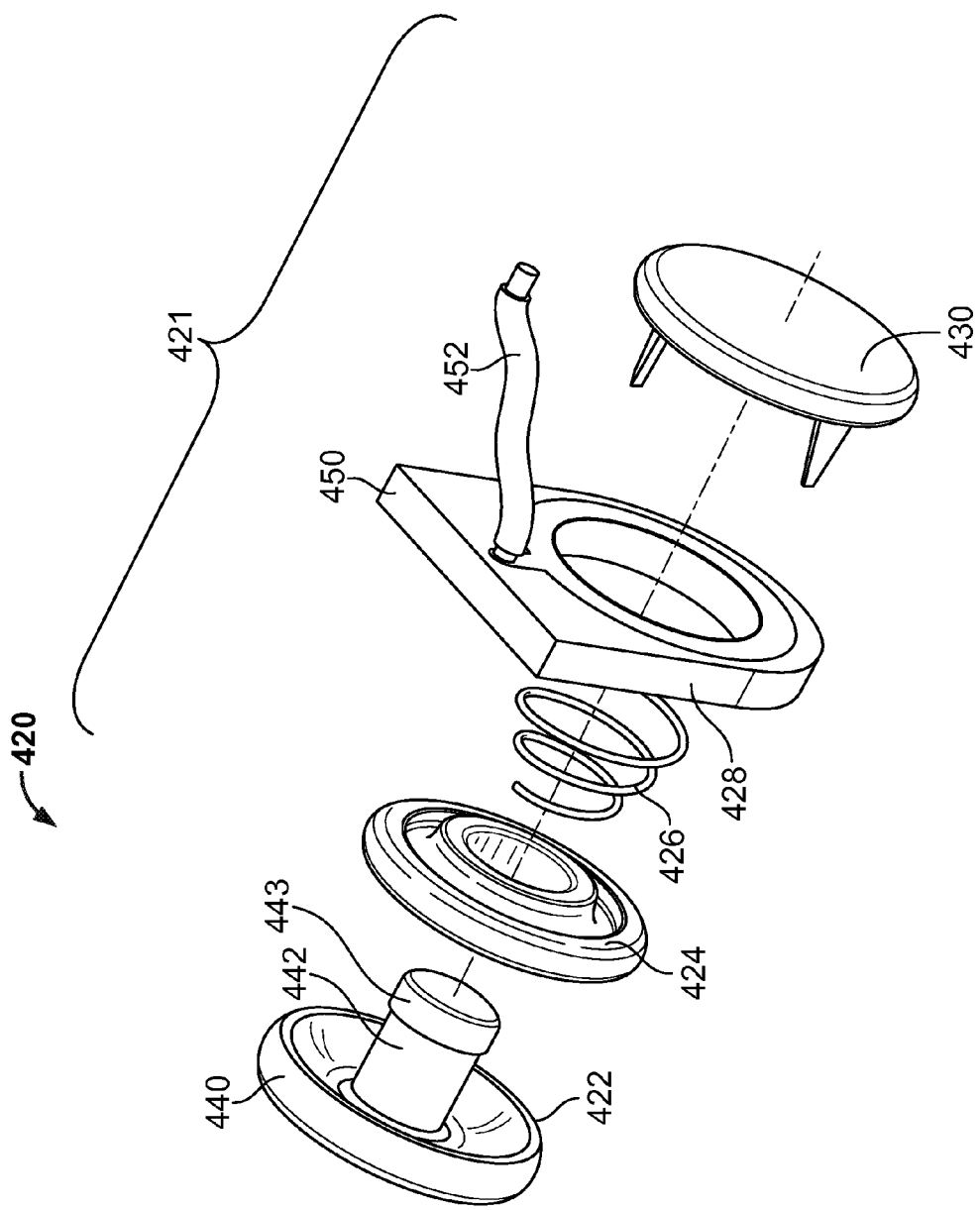
FIG. 4 is an embodiment illustrating an exploded assembly diagram of an electrode set.

FIG. 4 is an embodiment illustrating an exploded assembly diagram of an electrode set. As shown in FIG. 4, the electrode set 420 includes two separable parts including a base portion 421 and an electrode 422 in which the base portion and the electrode can be separated from each other, such as to remove and replace the electrode. The base portion includes a top cover 424, a biasing mechanism 426, such as a spring, a base 428, and a basement 430. The basement 430 with its teeth passes through the base 428, captures the biasing mechanism between the basement and the top cover 424, and secures itself (using the teeth) to the top cover 424. The basement 430 and the top cover 424 may be made out of a metal or any conductive material.

As shown in FIG. 4, the electrode 422, which is removable and replaceable, further includes an electrode cap portion 440 and an electrode post portion 442 with a retaining ridge 443. In one embodiment, the electrode 422 is contoured. In one embodiment, the electrode cap portion 440 is contoured. The electrode post portion 442 can be press fitted into the top cover 424 so that it engages the biasing mechanism 426 to bias the electrode away from the base 428 so that the retaining ridge 443 is pressed against the top cover. The biasing of the electrode away from the base 428 means that the electrode set 420, when assembled, can be pressed against the user's skin and the spring 426 will maintain a connection with the skin of the user. Accordingly, the electrode 422 is biased away from the base 428 which allows the electrode to pivot in any direction as well as rotate to accommodate the contours of the user's skin/head on which the electrode is placed, thereby maintaining flush contact with the skin/head of the user with the electrode (e.g., electrode 422 with contoured electrode cap portion 440). The is biasing of the electrode away from the base 428 also allows the assembled electrode set 420 to be pressed fitted against the skin of the user as the biasing mechanism can compress, but maintain the electrode set in a pressing relationship against the skin of the user.

In one embodiment, the electrode is a button type electrode that can be a silver-silver chloride surface electrode or a silver or gold plated surface electrode. The button type electrode can be a dry or wet (and/or disposable) electrode. In operation, the electrical current being generated based on the measured signal by the electrode passes through the electrode 422 (which is conductive) and the biasing mechanism 426 (which can be metal or conductive) to a connection 452. In the electrode set 420, the electrode 422 can have one or more different length electrode post portions 442 so that different pressures may be applied to the skin/head of the user. As also shown in FIG. 4, the base 428 also includes a set of circuitry 450, such as the circuits on a printed circuit board, and a connection 452, such as a wire, that connects the set of circuitry 450 (e.g., an ASIC) in the electrode set 420 to a bio-amplifier (not shown) so that a bioelectrical signal detected by the electrode 422 can be processed.

Figure 5:
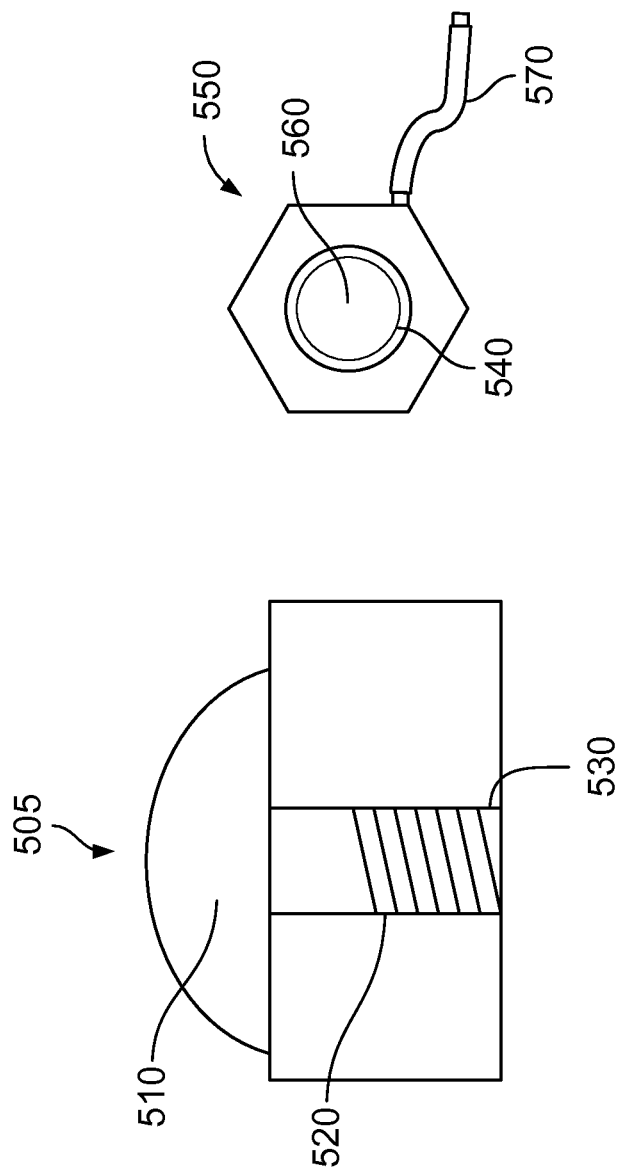
FIG. 5 is another embodiment illustrating an exploded assembly diagram of an electrode set.

FIG. 5 is another embodiment illustrating an exploded assembly diagram of an electrode set. As shown, in this embodiment, as an alternative to the spring assembly related mechanism of FIG. 4, an electrode assembly includes a screw 505 with a cap 510 and a post 520, which includes a spiral thread 530. In this example screw 505 connects to a base 550, which has an opening 560 with a retaining thread 540, whereby screw 505 can be connected to base 550 via spiral thread 530 and retaining thread 540 similar to a nut and bolt mechanism for securing the electrode set assembly to, for example, a sensor headset. Base 550 includes a connection 570, such as a wire, that connects circuitry (not shown) that is integrated and/or in electrical communication with the electrode set. In one embodiment, pivoting and rotation for an electrode is provided by a flexible forehead sensor arm connected to a sensor headset. In one embodiment, pivoting and rotation for an electrode is provided by a pivotable and rotatable ear piece connected to a sensor headset.

FIG. 6 is an embodiment of a contoured electrode illustrating a side view 610 and a top view 620 of a contoured electrode including a conductive fabric 635. As shown in is both side view 610 and top view 620, the contoured electrode includes a shaped protrusion 625 wrapped in conductive fabric 635. Referring to top view 620, a conductive thread 640 is connected to conductive fabric 635, and conductive thread 640 is connected to thread tie mechanism 650 for connecting to a connection wire 660.

FIG. 7 is another embodiment of a contoured electrode illustrating a side view 710 and a top view 720 of a contoured electrode including a conductive fabric 735. As shown in both side view 710 and top view 720, the contoured electrode includes a contoured riser 740 wrapped in conductive fabric 735. Also, as shown, a conductive wire loop 750 is connected to a connection wire 760.

FIG. 8 is another embodiment of a contoured electrode illustrating a side view 810 and a top view 820 of a contoured electrode including a conductive fabric 835. As shown in both side view 810 and top view 820, the contoured electrode includes a contoured metal plate 840 wrapped in conductive fabric 835 and connected to a connection wire 860.

Figure 9:
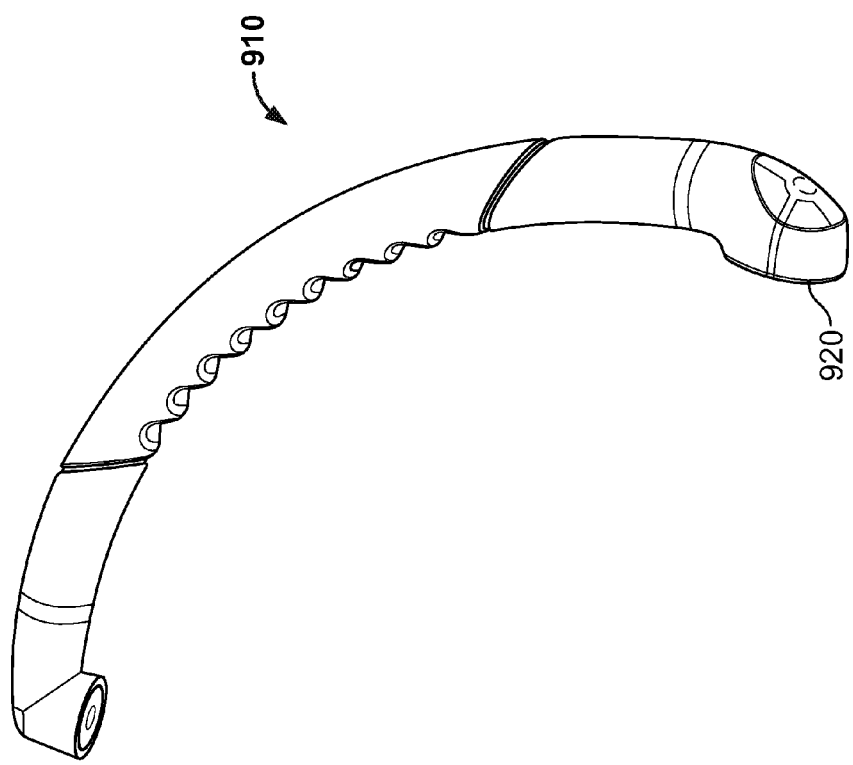
FIG. 9 is an embodiment of a forehead sensor arm.

FIG. 9 is an embodiment of a forehead sensor arm. As shown in FIG. 9, forehead sensor arm 910 includes an electrode signal sensor 920. In one embodiment, the forehead sensor arm 910 is flexible and also resilient enough to maintain the electrode signal sensor 920 in close, stable, and continual contact with the skin of the user's forehead. In one embodiment, the electrode signal sensor 920 is a contoured electrode (e.g., electrode set 420 as shown in FIG. 4).

FIG. 10 is an embodiment of a sensor headset. As shown in FIG. 10, a sensor headset 1000 includes a forehead sensor arm 1010, which includes an electrode signal sensor 720. In one embodiment, the forehead sensor arm 1010 is flexible and also resilient enough to maintain the electrode signal sensor 1020 in close, stable, and continual contact with the skin of the user's forehead. Sensor headset 1000 also includes various headset controls (e.g., an on/off—power button and other headset controls) 1030 and includes various audio controls (e.g., play, pause, rewind, and fast forward) 1040. In one embodiment, the electrode signal sensor 1020 is a contoured electrode (e.g., electrode set 420 as shown in FIG. 4). In one embodiment, a sensor headset integrates a contoured electrode in the earpiece.

Although the foregoing embodiments have been described in some detail for is purposes of clarity of understanding, the invention is not limited to the details provided. There are many alternative ways of implementing the invention. The disclosed embodiments are illustrative and not restrictive.

What is claimed is:

1. An apparatus for a bioelectrical signal sensor, comprising:
a headset, wherein a holder is connected to the headset, and wherein the holder is pivotable and rotatable; and
a contoured bioelectrical signal sensor connected to the holder, wherein the contoured bioelectrical signal sensor comprises an electrode set;
wherein the electrode set comprises:
a contoured electrode with a protruding shape for maintaining contact with a user's head;
a base comprising a conductive biasing mechanism, an opening, and a connection; and
wherein the contoured electrode comprises a cap portion with the protruding shape for maintaining contact with the user's head and a post portion protruding out of a side of the cap portion opposite the protruding shape, the post portion having a retaining ridge, wherein the cap portion with the protruding shape and the post are electrically connected.

2. The apparatus for a bioelectrical signal sensor as recited in claim 1, wherein the contoured electrode is a dry electrode.

3. The apparatus for a bioelectrical signal sensor as recited in claim 1, wherein the electrode set further comprises:
wherein the contoured electrode is inserted into the opening of the base, wherein the contoured electrode is releasably retained in the base by the retaining ridge, and wherein the post portion having the retaining ridge of the contoured electrode engages the biasing mechanism and electrically connects to the biasing mechanism, so that a signal detected by the contoured electrode passes through the contoured electrode and electrically connected biasing mechanism to the connection and the contoured electrode is pivotable and rotatable in the opening of the base.

4. The apparatus for a bioelectrical signal sensor as recited in claim 1, wherein the headset includes an audio speaker and a plurality of audio controls, and wherein the holder is an integrated component of the headset.

5. The apparatus for a bioelectrical signal sensor as recited in claim 1, wherein the holder is connected to a flexible arm, wherein the flexible arm is connected to the headset.

6. The apparatus for a bioelectrical signal sensor as recited in claim 1, wherein the protruding shape of the contoured electrode is a spherical shape.

7. The apparatus for a bioelectrical signal sensor as recited in claim 1, wherein a shape of the contoured electrode is selected from the group consisting of a spherical shape, a half spherical shape, a quarter spherical shape, a teardrop shape, an elliptical shape, and a rectangular shape.

8. The apparatus for a bioelectrical signal sensor as recited in claim 1, wherein the contoured electrode is a dry electrode, and wherein:
the electrode is inserted into the opening of the base, wherein the electrode is releasably retained in the base by the retaining ridge, and wherein the electrode is pivotable and rotatable in the opening of the base; and
wherein a signal detected by the electrode passes through the conductive electrode and the conductive biasing mechanism to the connection.

9. The apparatus for a bioelectrical signal sensor as recited in claim 1, wherein the contoured electrode is a dry electrode, and wherein:
the electrode is inserted into the opening of the base, wherein the electrode is releasably retained in the base by the retaining ridge, and wherein the electrode is pivotable and rotatable in the opening of the base; and
wherein a signal detected by the electrode passes through the conductive electrode and the conductive biasing mechanism to the connection, and wherein the electrode is replaceable.

10. The apparatus for a bioelectrical signal sensor as recited in claim 1, wherein the contoured electrode comprises a conductive fabric that is wrapped around the protruding shape of the contoured electrode.

11. The apparatus for a bioelectrical signal sensor as recited in claim 1, wherein the contoured electrode is a dry electrode, wherein the contoured electrode comprises a conductive fabric that is wrapped around the protruding shape of the contoured electrode, and wherein the electrode set further comprises:
the base having a contoured shape; and
an electrical connection, wherein the electrical connection connects the conductive fabric to a connection wire.

12. The apparatus for a bioelectrical signal sensor as recited in claim 1, wherein the contoured electrode is a dry electrode, wherein the contoured electrode comprises a conductive fabric that is wrapped around the protruding shape of the contoured electrode, and wherein the electrode set further comprises:

the base having a contoured shape; and an electrical connection, wherein the electrical connection connects the conductive fabric to a connection wire, and wherein the electrical connection is selected from the group consisting of a metal riser, a metal wire loop, and a conductive thread with a thread tie post for connecting the conductive fabric to the connection wire.

13. An apparatus for a bioelectrical signal sensor, comprising:

a headset, wherein a holder is connected to the headset, and wherein the holder is pivotable and rotatable; and a contoured bioelectrical signal sensor connected to the holder, wherein the contoured bioelectrical signal sensor comprises an electrode set;

wherein the electrode set comprises:

a contoured electrode with a protruding shape for maintaining contact with a user's head;

a base having an opening and a connection;

the contoured electrode having a cap portion and a post portion connected to the cap portion, the post portion having a spiral screw thread;

the contoured electrode is screwed into the opening of the base, wherein the contoured electrode is releasably retained in the base by a retaining spiral screw thread in the opening of the base; and wherein a signal detected by the contoured electrode passes through the cap portion to the post portion and the base to the connection.

14. The apparatus for a bioelectrical signal sensor as recited in claim 13, wherein the protruding shape of the contoured electrode is a spherical shape.

15. The apparatus for a bioelectrical signal sensor as recited in claim 13, wherein the contoured electrode comprises a conductive fabric that is wrapped around the protruding shape of the contoured electrode.

16. The apparatus for a bioelectrical signal sensor as recited in claim 13, wherein the contoured electrode is a dry electrode, wherein the contoured electrode comprises a conductive fabric that is wrapped around the protruding shape of the contoured electrode, wherein the connection connects the conductive fabric to a connection wire.

17. The apparatus for a bioelectrical signal sensor as recited in claim 13, wherein the contoured electrode is a dry electrode, wherein the contoured electrode comprises a conductive fabric that is wrapped around the protruding shape of the contoured electrode, and wherein the electrode set further comprises:

the base having a contoured shape; and wherein the connection connects the conductive fabric to a connection wire.

18. The apparatus for a bioelectrical signal sensor as recited in claim 13, wherein the contoured electrode is a dry electrode, wherein the contoured electrode comprises a conductive fabric that is wrapped around a contoured shape of the contoured electrode, and wherein the electrode set further comprises:

the base having a contoured shape; and wherein the connection connects the conductive fabric to a connection wire, and wherein the connection is selected from the group consisting of a metal riser, a metal wire loop, and a conductive thread with a thread tie post for connecting the conductive fabric to the connection wire.

19. An apparatus for a bioelectrical signal sensor, comprising:

a holder, wherein the holder houses one or more bioelectrical signal sensors;

a bioelectrical signal sensor connected to the holder, wherein the bioelectrical signal sensor comprises an electrode, and wherein the electrode is a dry electrode wrapped in a conductive fabric;

an electrode assembly, wherein the electrode assembly includes a screw and a nut for connecting the electrode assembly to the holder; and an electrode set, wherein the electrode set includes the electrode, and wherein the electrode set further comprises:

a base having an opening and a connection;

the electrode having a cap portion and a post portion connected to the cap portion, the post portion having a spiral screw thread;

the electrode is screwed into the opening of the base wherein the electrode is releasably retained in the base by a retaining spiral screw thread in the opening of the base; and wherein a signal detected by the electrode passes through the cap portion to the post portion and the base to the connection.

20. The apparatus for a bioelectrical signal sensor as recited in claim 19, further comprising:

a headset, wherein the headset includes an audio speaker and a plurality of audio controls, and wherein the holder is an integrated component of the headset.

21. The apparatus for a bioelectrical signal sensor as recited in claim 19, further comprising:

a headset, wherein the holder is integrated in an earpiece of the headset.

22. The apparatus for a bioelectrical signal sensor as recited in claim 19, wherein the electrode is a contoured electrode.

23. The apparatus for a bioelectrical signal sensor as recited in claim 19, wherein the electrode is a shaped electrode, and wherein the shape of the electrode is selected from the group consisting of a spherical shape, a half spherical shape, a quarter spherical shape, a teardrop shape, an elliptical shape, and a rectangular shape.

* * * * *

UNITED STATES PATENT AND TRADEMARK OFFICE
CERTIFICATE OF CORRECTION

PATENT NO.        : 8,812,075 B2
APPLICATION NO.   : 13/620039
DATED             : August 19, 2014
INVENTOR(S)       : Nguyen et al.

It is certified that error appears in the above-identified patent and that said Letters Patent is hereby corrected as shown below:

In the claims

In column 6, line 3, claim 3 after "claim 1," delete "wherein the electrode set further comprises:"

Signed and Sealed this
Twenty-fourth Day of May, 2016

Michelle K. Lee
*Director of the United States Patent and Trademark Office*